US010028727B2

(12) United States Patent
Inoue

(10) Patent No.: US 10,028,727 B2
(45) Date of Patent: Jul. 24, 2018

(54) ULTRASOUND DIAGNOSTIC APPARATUS AND METHOD OF DISPLAYING ULTRASOUND IMAGE

(71) Applicant: HITACHI, LTD., Chiyoda-ku, Tokyo (JP)

(72) Inventor: Shinsuke Inoue, Kodaira (JP)

(73) Assignee: HITACHI, LTD., Tokyo (JP)

( * ) Notice: Subject to any disclaimer, the term of this patent is extended or adjusted under 35 U.S.C. 154(b) by 366 days.

(21) Appl. No.: 14/650,397

(22) PCT Filed: Nov. 28, 2013

(86) PCT No.: PCT/JP2013/082060
§ 371 (c)(1),
(2) Date: Jun. 8, 2015

(87) PCT Pub. No.: WO2014/087919
PCT Pub. Date: Jun. 12, 2014

(65) Prior Publication Data
US 2015/0297187 A1    Oct. 22, 2015

(30) Foreign Application Priority Data
Dec. 6, 2012 (JP) .................. 2012-267036

(51) Int. Cl.
*A61B 8/08* (2006.01)
*A61B 8/00* (2006.01)
(Continued)

(52) U.S. Cl.
CPC .............. *A61B 8/485* (2013.01); *A61B 8/085* (2013.01); *A61B 8/461* (2013.01); *A61B 8/466* (2013.01);
(Continued)

(58) Field of Classification Search
CPC ......... A61B 8/085; A61B 8/461; A61B 8/466; A61B 8/469; A61B 8/483; A61B 8/485;
(Continued)

(56) References Cited

U.S. PATENT DOCUMENTS

| 2007/0112270 | A1* | 5/2007 | Waki | ..................... A61B 8/08 600/455 |
| 2008/0208053 | A1* | 8/2008 | Hashimoto | ......... G01S 15/8993 600/441 |
| 2012/0287156 | A1 | 11/2012 | Tsujita | |

FOREIGN PATENT DOCUMENTS

| EP | 2502566 A1 | 9/2012 |
| JP | 2012-213545 A | 11/2012 |

(Continued)

OTHER PUBLICATIONS

Engel et al., Real-Time Volume Graphics, 2006, A. K. Peters, Ltd. Chapter 8.*

(Continued)

*Primary Examiner* — Katherine Fernandez
*Assistant Examiner* — Yi-Shan Yang
(74) *Attorney, Agent, or Firm* — Oliff PLC

(57) ABSTRACT

Shading of a site other than a site of interest is disabled to allow construction of a visually good three-dimensional image even when the site other than the site of interest is displayed in a translucent manner. An ultrasound diagnostic apparatus includes a sending section that sends an ultrasonic wave to a diagnosing object via an ultrasound probe, a receiving section that receives a reflected echo signal from the diagnosing object, a three-dimensional elasticity image constructing section that performs volume rendering with shading on elasticity volume data with an elasticity value based on the reflected echo signal to construct a three-dimensional elasticity image, and an image display section that displays the three-dimensional elasticity image. The (Continued)

three-dimensional elasticity image constructing section performs the volume rendering using an elasticity opacity according to the elasticity value and disables the shading of a portion with the elasticity opacity with a predetermined value.

16 Claims, 15 Drawing Sheets

(51) Int. Cl.
    *G06T 1/00*      (2006.01)
    *G01S 7/52*      (2006.01)
    *G06T 7/00*      (2017.01)
    *G06T 15/80*      (2011.01)
    *G06T 7/11*      (2017.01)
    *G01S 15/89*      (2006.01)

(52) U.S. Cl.
    CPC .............. *A61B 8/469* (2013.01); *A61B 8/483* (2013.01); *A61B 8/5207* (2013.01); *A61B 8/5238* (2013.01); *G01S 7/52042* (2013.01); *G01S 7/52071* (2013.01); *G06T 1/00* (2013.01); *G06T 7/0012* (2013.01); *G06T 7/11* (2017.01); *G06T 15/80* (2013.01); *G01S 15/8993* (2013.01); *G06T 2200/04* (2013.01); *G06T 2207/10136* (2013.01); *G06T 2207/30004* (2013.01); *G06T 2207/30196* (2013.01); *G06T 2210/41* (2013.01)

(58) Field of Classification Search
    CPC . A61B 8/5207; A61B 8/5238; G01S 15/8993; G01S 7/52042; G01S 7/52071; G06T 15/80; G06T 1/00; G06T 2200/04; G06T 2207/10136; G06T 2207/30004; G06T 2207/30196; G06T 2210/41; G06T 7/0012

See application file for complete search history.

(56) References Cited

FOREIGN PATENT DOCUMENTS

| WO | WO 2011062106 A1 | * | 5/2011 | ............... A61B 8/08 |
|---|---|---|---|---|
| WO | 2011/086774 A1 | | 7/2011 | |
| WO | WO 2011086774 A1 | * | 7/2011 | ............... A61B 8/08 |
| WO | WO 2011099410 A1 | * | 8/2011 | ............... A61B 8/06 |
| WO | 2012/043200 A1 | | 4/2012 | |

OTHER PUBLICATIONS

OsiriX User Manual, 2011, Section 7.*
Levoy. "Volume Rendering: Display of Surfaces from Volume Data". IEEE Computer Graphics & Applications, May 1988, pp. 30-37.*
Jan. 21, 2014 Search Report issued in International Patent Application No. PCT/JP2013/082060.
Jan. 21, 2014 Written Opinion issued in International Patent Application No. PCT/JP2013/082060.
Jul. 25, 2016 Extended Search Report issued in European Patent Application No. 13860332.9.
Boctor, Emad M., et al., "Elasticity-Based Three Dimensional Ultrasound Real-Time Volume Rendering," Proceedings of SPIE, vol. 7261, Feb. 26, 2009, pp. 72612V-1-72612V-9.

* cited by examiner

ULTRASOUND DIAGNOSTIC APPARATUS AND METHOD OF DISPLAYING ULTRASOUND IMAGE

TECHNICAL FIELD

The present invention relates to an ultrasound diagnostic apparatus and a method of displaying an ultrasound image, and in particular, to an ultrasound diagnostic apparatus and a method of displaying an ultrasound image in which shading of a predetermined portion is disabled.

BACKGROUND ART

An ultrasound diagnostic apparatus sends an ultrasonic wave to an inside of a diagnosing object via an ultrasound probe, and based on a received signal received from a biological tissue inside the diagnosing object, constructs a three-dimensional cross-section region image and a three-dimensional elasticity image to display an ultrasound image.

In order to appropriately display a site of interest even when a site other than the site of interest is present on a point-of-view side with respect to the site of interest in a line-of-sight direction, conventional ultrasound diagnostic apparatuses set a larger opacity for the site of interest and a smaller opacity for the site other than the site of interest when constructing a three-dimensional elasticity image (for example, see Patent Literature 1).

CITATION LIST

Patent Literature

Patent Literature 1: WO2011/086774

SUMMARY OF INVENTION

Technical Problem

Patent Literature 1 discloses the setting of the opacity of the three-dimensional elasticity image, but does not disclose that shading in volume rendering is disabled based on the opacity or an elasticity value. Thus, even when the opacity is set to a smaller value to display the site other than the site of interest in a translucent manner, the shading is also executed on the translucent site (site other than the site of interest), possibly making the three-dimensional elasticity image visually bad.

An object of the present invention is to disable the shading of the site other than the site of interest to construct a visually good three-dimensional elasticity image even when the site other than the site of interest is displayed in a translucent manner.

Solution to Problem

An ultrasound diagnostic apparatus in the present invention includes a sending section that sends an ultrasonic wave to a diagnosing object via an ultrasound probe, a receiving section that receives a reflected echo signal from the diagnosing object, a three-dimensional elasticity image constructing section that performs volume rendering with shading on elasticity volume data with an elasticity value based on the reflected echo signal to construct a three-dimensional elasticity image, and an image display section that displays the three-dimensional elasticity image. The three-dimensional elasticity image constructing section performs the volume rendering using an elasticity opacity according to the elasticity value and disables the shading of a portion with the elasticity opacity with a predetermined value.

This configuration disables the shading of the site other than the site of interest to allow a visually good three-dimensional elasticity image to be constructed even when a site other than a site of interest is displayed in a translucent manner.

Advantageous Effects of Invention

The ultrasound diagnostic apparatus according to the present invention disables the shading in the volume rendering based on the elasticity opacity or the elasticity value, allowing a visually good three-dimensional elasticity image to be constructed.

DESCRIPTION OF EMBODIMENTS

First Embodiment

Figure 1:
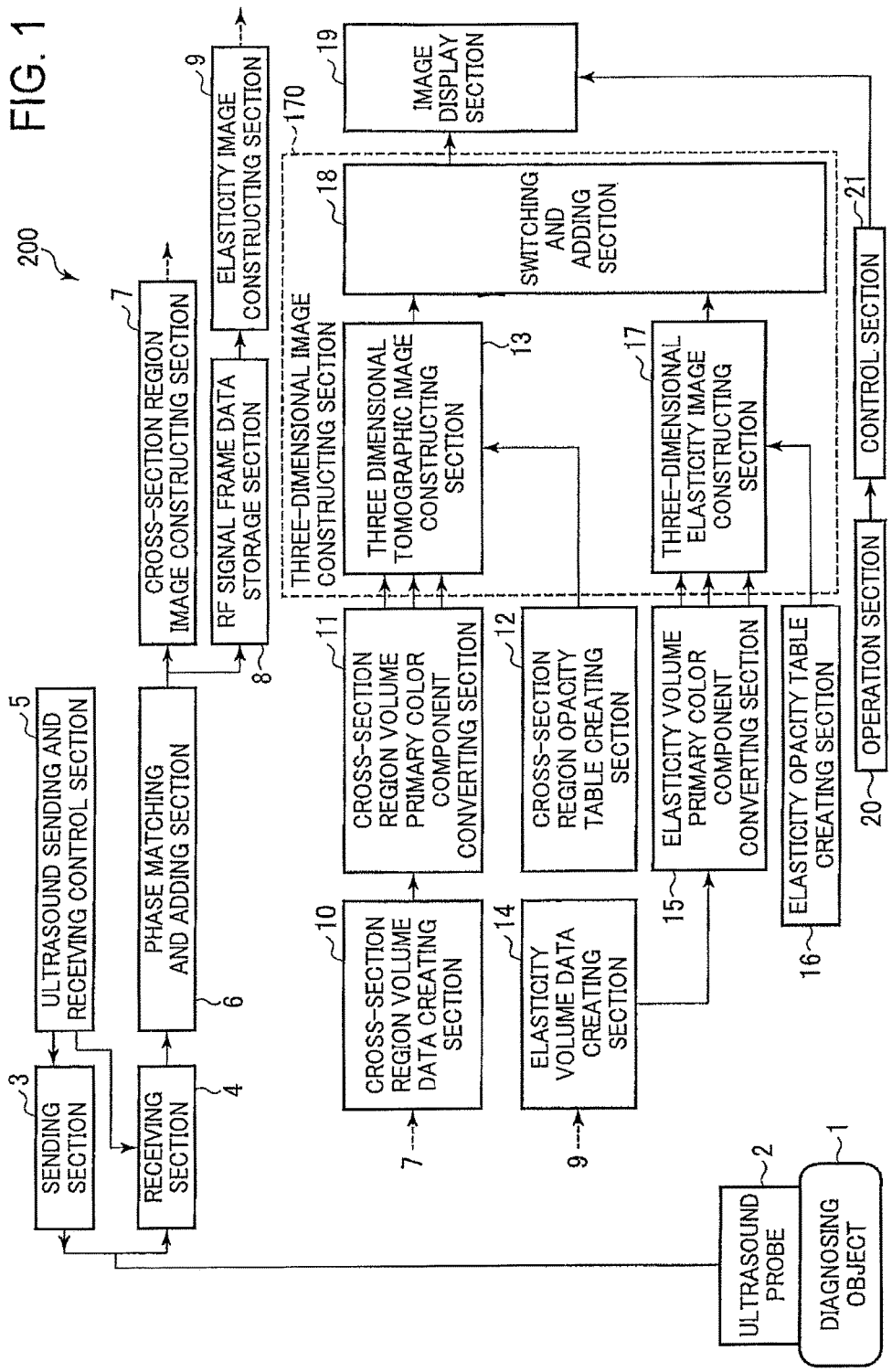
FIG. 1 is a diagram depicting an example of an ultrasound diagnostic apparatus according to a first embodiment.

An ultrasound diagnostic apparatus according to an embodiment of the present invention will be described with reference to the drawings. FIG. 1 is a diagram depicting an example of the ultrasound diagnostic apparatus according to the present embodiment. As depicted in FIG. 1, a feature of an ultrasound diagnostic apparatus 200 in the present embodiment is such that the ultrasound diagnostic apparatus 200 includes a sending section 3 that sends an ultrasonic wave to a diagnosing object 1 via an ultrasound probe 2, a receiving section 4 that receives a reflected echo signal from the diagnosing object 1, a three-dimensional elasticity image constructing section that performs volume rendering with shading on elasticity volume data with an elasticity value based on the reflected echo signal to construct a three-dimensional elasticity image, and an image display section 19 that displays the three-dimensional elasticity image and such that the three-dimensional elasticity image constructing section 17 performs the volume rendering using an elasticity opacity according to the elasticity value and disables the shading of a portion with the elasticity opacity with a predetermined value.

Furthermore, another feature of the ultrasound diagnostic apparatus 200 according to the present embodiment is such that the ultrasound diagnostic apparatus 200 includes the sending section 3 that sends an ultrasonic wave to the diagnosing object 1 via the ultrasound probe 2, the receiving section 4 that receives a reflected echo signal from the diagnosing object 1, the three-dimensional elasticity image constructing section 17 that performs volume rendering with shading on elasticity volume data with an elasticity value based on the reflected echo signal to construct a three-dimensional elasticity image, and the image display section 19 that displays the three-dimensional elasticity image and such that the three-dimensional elasticity image constructing section 17 disables the shading of a portion with the elasticity value of a predetermined value.

The ultrasound diagnostic apparatus 200 in the present embodiment will be described in detail. The ultrasound diagnostic apparatus 200 includes the ultrasound probe 2 that is brought into abutting contact with the diagnosing object 1 for use, the sending section 3 that repeatedly sends an ultrasonic wave to the diagnosing object 1 at given time intervals via the ultrasound probe 2, the receiving section 4 that receives the reflected echo signal reflected from the diagnosing object 1, an ultrasound sending and receiving control section 5 that controls the sending section 3 and the receiving section 4, and a phase matching and adding section 6 that subjects reflected echoes received by the receiving section 4 to phase matching and adds the resultant reflected echoes together.

The ultrasound probe 2 is formed to include a plurality of transducers disposed therein and has a function to send and receive an ultrasonic wave to and from the diagnosing object 1 via the transducers. The ultrasound probe 2 includes a plurality of rectangular or fan-shaped transducers and can mechanically vibrate the transducers in a direction orthogonal to an arrangement direction of the plurality of transducers to three-dimensionally send and receive an ultrasonic wave. The ultrasound probe 2 may include a plurality of two-dimensionally arranged transducers to enable sending and receiving of an ultrasonic wave to be electronically controlled.

The sending section 3 generates a send pulse that drives the transducers to generate an ultrasonic wave. The sending section 3 has a function to set a convergent point of the sent ultrasonic wave to a predetermined depth. The receiving section 4 amplifies a reflected echo signal received by the ultrasound probe 2 at a predetermined gain to generate an RF signal (that is, a received signal). The ultrasound sending and receiving control section 5 controls the sending section 3 and the receiving section 4.

The phase matching and adding section 6 controls the phase of an RF signal amplified by the receiving section 4 to form an ultrasound beam with respect to one or more convergent points, generating RF signal frame data (corresponding to RAW data).

The ultrasound diagnostic apparatus 200 includes a cross-section region image constructing section 7 that constructs a two-dimensional cross-section region image based on the RF signal frame data generated by the phase matching and adding section 6, a cross-section region volume data creating section 10 that performs a three-dimensional coordinate conversion on the two-dimensional cross-section region image constructed by the cross-section region image constructing section 7 based on an acquisition position of the two-dimensional cross-section region image to generate cross-section region volume data, a cross-section region volume primary color component converting section 11 that separates (converts) the cross-section region volume data into three primary color components for color image display corresponding to luminance, a cross-section region opacity table creating section (cross-section region opacity setting section) 12 that creates a table of cross-section region opacity corresponding to the luminance of the cross-section region volume data, a three-dimensional cross-section region image constructing section 13 that perform, using cross-section region opacity, volume rendering on the volume data on the primary color components in the cross-section region volume data resulting from the separation (conversion) by the cross-section region volume primary color component converting section 11, to construct a three-dimensional cross-section region image, an RF signal frame data storage section 8 that stores the RF signal frame data generated by the phase matching and adding section 6, an elasticity image constructing section 9 that constructs a two-dimensional elasticity image based on a plurality of RF signal frame data stored in the RF signal frame data storage section 8, an elasticity volume data creating section 14 that performs a three-dimensional coordinate conversion on the two-dimensional elasticity image constructed by the elasticity image constructing section 9 based on an acquisition position of the two-dimensional elasticity image to generate elasticity volume data, an elasticity volume primary color component converting section 15 that separates (converts) the elasticity volume data into three primary color components for color image display corresponding to the elasticity value, an elasticity opacity table creating section (elasticity opacity setting section) 16 that creates a table of elasticity opacity corresponding to the elasticity value for the elasticity volume data, the three-dimensional elasticity image constructing section 17 that performs volume rendering, using the elasticity opacity, on the volume data on the respective primary color components in the elasticity volume data resulting from the separation (conversion) by the elasticity volume primary color component converting section 15 to construct a three-dimensional elasticity image, a switching and adding section 18 that synthesizes a two-dimensional cross-section region image and a two-dimensional elasticity image or synthesizes a three-dimensional cross-section region image and a three-dimensional elasticity image, and the image display section 19 that displays synthetic images resulting from the synthesis by the switching and adding section 18, two-dimensional images (two-dimensional cross-section region images and two-dimensional elasticity images), three-dimensional images (three-dimensional cross-section region images and three-dimensional elasticity images), and the like.

The three-dimensional cross-section region image constructing section 13, the three-dimensional elasticity image constructing section 17, and the switching and adding section 18 are included in a three-dimensional image constructing section 170. In performing the volume rendering with shading on the volume data, the three-dimensional image constructing section 170 disables the shading of a portion with at least one of a predetermined elasticity opacity according to the elasticity value and a predetermined elasticity value to construct a three-dimensional image.

Furthermore, the ultrasound diagnostic apparatus 200 includes a control section 21 that controls the respective components and an operation section 20 that provides various inputs to the control section 21. The operation section 20 includes a keyboard, a trackball and the like.

Based on set conditions of the control section 21, the cross-section region image constructing section 7 receives the RF signal frame data output by the phase matching and adding section 6 and executes signal processing such as gain correction, log compression, detection, contour emphasis, filter processing and the like to construct a two-dimensional cross-section region image.

The ultrasound probe 2 can send and receive an ultrasonic wave and measure a declination angle (θ, Ø) in a sending and receiving direction. Based on the declination angle (θ, Ø) in the sending and receiving direction corresponding to the acquisition position of the two-dimensional cross-section region image, the cross-section region volume data creating section 10 performs a three-dimensional conversion on a plurality of two-dimensional cross-section region images to generate (create) cross-section region volume data.

The cross-section region volume primary color component converting section 11 converts the cross-section region volume data into a plurality of primary color components. The cross-section region volume primary color component converting section 11 separates (converts) the cross-section region volume data into three primary color components for color image display corresponding to the luminance value to output the volume data on each primary color component. The three primary color components for color image display are preferably the three primary colors R (red), G (green), and B (blue) that determine a hue. However, instead of these components, the cross-section region volume primary color component converting section 11 may separate (convert) the cross-section region volume data into other primary color components.

In the present embodiment, an example will be described in which the cross-section region volume data is separated (converted) into the RGB three primary colors. The cross-section region image is generally displayed in black and white. Hues are assigned in accordance with the luminance such that a portion with the highest luminance is displayed in white, whereas a portion with the lowest luminance is displayed in black. For example, in terms of the RGB three primary colors, white is represented by R=255, G=255, and B=255. Thus, a voxel with the highest luminance can be separated (converted) into three components, R=255, G=255, and B=255. Thus, for each voxel in the cross-section region volume data, the cross-section region volume primary color component converting section 11 separates (converts) the hue according to the luminance into three RGB components to create an R component as cross-section region first component volume data, a G component as cross-section region second component volume data, and a B component as cross-section region third component volume data.

Figure 2:
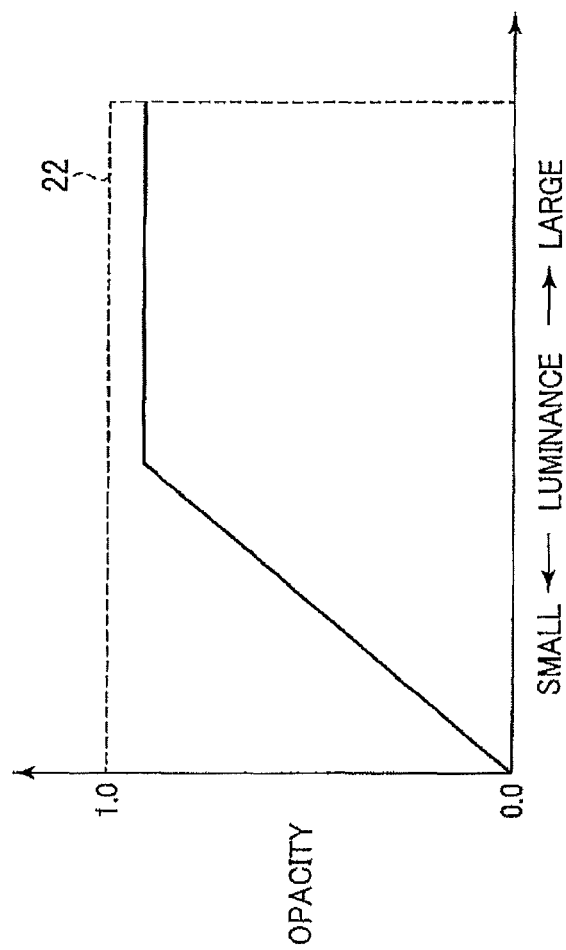
FIG. 2 is a diagram depicting a cross-section opacity according to a luminance value.

FIG. 2 is a diagram depicting the cross-section region opacity according to the luminance value. The three-dimensional cross-section region image constructing section 13 performs the volume rendering using the cross-section region opacity according to the luminance value. The cross-section region opacity table creating section (cross-section region opacity setting section) 12 associates the luminance value with the cross-section region opacity to set the cross-section region opacity according to the luminance value.

As depicted in FIG. 2, the cross-section region opacity table creating section (cross-section region opacity setting section) 12 creates a cross-section region opacity table 22 in which the axis of abscissas represents the luminance value for the cross-section region volume data and in which the axis of ordinate represents the opacity. The three-dimensional cross-section region image constructing section 13 uses the opacity set in the cross-section region opacity table 22 as the cross-section region opacity.

Figure 3:
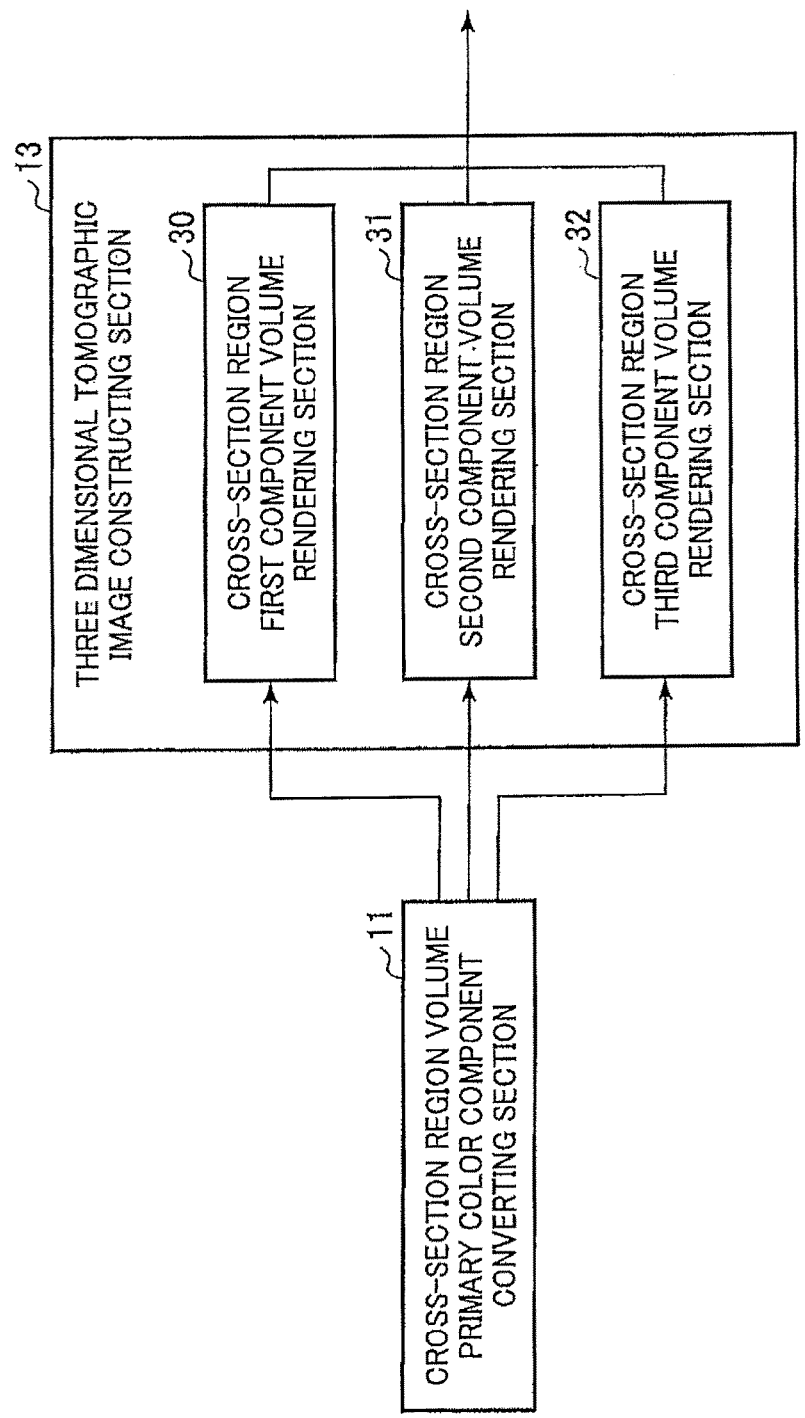
FIG. 3 is a diagram depicting an example of a three-dimensional cross-section region image constructing section.

FIG. 3 is a diagram depicting an example of the three-dimensional cross-section region image constructing section 13. As depicted in FIG. 3, the three-dimensional cross-section region image constructing section 13 includes a cross-section region first component volume rendering section 30, a cross-section region second component volume rendering section 31, and a cross-section region third component volume rendering section 32. The cross-section region first component volume rendering section 30 performs the volume rendering with shading on cross-section region first component volume data. The cross-section region second component volume rendering section 31 performs the volume rendering with shading on cross-section region second component volume data. The cross-section region third component volume rendering section 32 performs the volume rendering with shading on cross-section region third component volume data.

The volume rendering with shading is performed using Expressions (1) to (3). The three-dimensional cross-section region image constructing section 13 creates a three-dimensional cross-section region image by combining (synthesizing) the results of the volume rendering with shading performed on the volume data on the respective components (for example, RGB components).

$$C_{out}(i) = C_{out}(i-1) + (1 - A_{out}(i-1)) \cdot A(i) \cdot C(i) \cdot S(i) \quad (1)$$

$$A_{out}(i) = A_{out}(i-1) + (1 - A_{out}(i-1)) \cdot A(i) \quad (2)$$

$$A(i) = \text{Opacity}[I(i)] \quad (3)$$

C(i) designates a component value of an "i"th voxel on the line of sight when a three-dimensional cross-section region image is viewed at a predetermined point on a two-dimensional plane of projection (three-dimensional cross-section region image) to be created. In the present embodiment, C(i) is the value of each primary color component (for example, each of RGB primary color component values) in a voxel. Cout(i) designates an output pixel value. For example, when N voxels are arranged on the line of sight, Cout(N−1) designates a primary color component value resulting from integration of the primary color component values "C(i=0)" to "C(i=N−1)". Cout(N−1) is a finally output pixel value. Cout(i−1) designates a component value (primary color component value) resulting from integration of the values up to the "i−1"th value.

I(i) designates the luminance value of the "i"th voxel on the line of sight when the three-dimensional cross-section region image is viewed at the predetermined point on the two-dimensional plane of projection (three-dimensional cross-section region image) to be created. A(i) designates the opacity (cross-section region opacity) according to the "i"th luminance value I(i) on the line of sight, and is set in the cross-section region opacity table 22 with a value ranging from "0" to "1.0" as depicted in FIG. 2. The cross-section region opacity determines the rate of contribution to the output two-dimensional plane of projection (three-dimensional cross-section region image). Aout(i−1) designates the opacity (cross-section region opacity) integrated each time the voxel is passed through, and is an integral value of the opacities (cross-section region opacities) up to the "i−1"th opacity.

S(i) designates a shading weight component for the shading determined by a gradient calculated from the luminance value I(i) and peripheral luminance values. For example, when the direction of a light beam from a light source aligns with a normal direction in a plane around a voxel "i", the light beam is most significantly reflected, and thus, a shading weight component "S(i)=1.0" is provided. When the direction of the light source is orthogonal to the normal direction, the light beam is most insignificantly reflected, and thus, a shading weight component "S(i)=0.0" is provided. Thus, the shading weight component S(i) exhibits a shading effect.

Both Cout(i) and Aout(i) have an initial value of "0". As illustrated in Expression (2), Aout(i) is integrated each time the voxel is passed through, and converges to "1.0". Hence, as illustrated in Expression (1), when the integral value of the opacities up to the "i−1"th opacity is "1.0" (Aout(i−1) ≈1.0), the "i"th and subsequent component values C(i) are not reflected in the output image.

As described above, the three-dimensional cross-section region image constructing section 13 performs the volume rendering with shading on at least one of the plurality of primary color components to construct a three-dimensional cross-section region image.

The elasticity image constructing section 9 measures displacement based on a plurality of RF signal frame data stored in the RF signal frame data storage section 8. The elasticity image constructing section 9 calculates the elasticity value based on the measured displacement to construct a two-dimensional elasticity image. The elasticity value is at least one of pieces of elasticity information such as strain, a modulus of elasticity, displacement, viscosity, and a strain ratio.

The elasticity volume data creating section 14 performs a three-dimensional conversion on a plurality of two-dimensional elasticity images based on the declination angle (θ, Ø) in the sending and receiving direction corresponding to the acquisition position of the two-dimensional elasticity image to generate (create) elasticity volume data.

Figure 4:
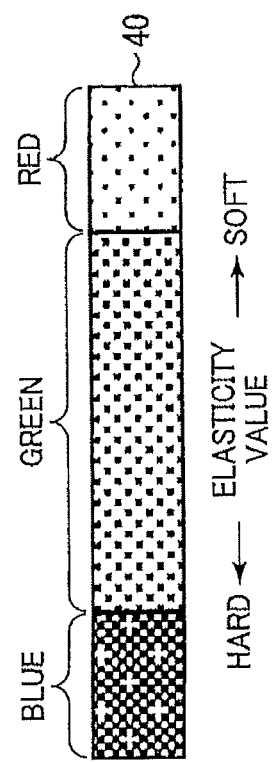
FIG. 4 is a diagram depicting an example of a hue bar according to an elasticity value.

The elasticity volume primary color component converting section 15 converts the elasticity volume data into a plurality of primary color components. The elasticity volume primary color component converting section 15 separates (converts) the elasticity volume data into the three primary color components for color image display corresponding to the elasticity value to output the volume data on each primary color component. FIG. 4 depicts an example of a hue bar according to the elasticity value. As depicted in FIG. 4, a blue hue, a green hue, and a red hue according to the elasticity value are assigned based on a hue bar 40 to allow the image display section 19 to display an elasticity image. For example, the blue hue is assigned to a hard site (site with a small elasticity value), and the red hue is assigned to a soft site (site with a large elasticity value). In the example in FIG. 4, the hues are discretely assigned. However, the hues may be assigned from a hard side (side with small elasticity values) to a soft side (side with large elasticity values) based on gradation ranging from blue to red. For example, the hues may be assigned so as to continuously vary from the hard side (side with small elasticity values) to the soft side (side with large elasticity values) by gradation, that is, from blue through aqua, green, and yellow to red.

For each voxel in the elasticity volume data, the elasticity volume primary color component converting section 15 separates (converts) the hue assigned according to the elasticity value into three RGB components to create an R component as elasticity first component volume data, a G component as elasticity second component volume data, and a B component as elasticity third component volume data.

Figure 5:
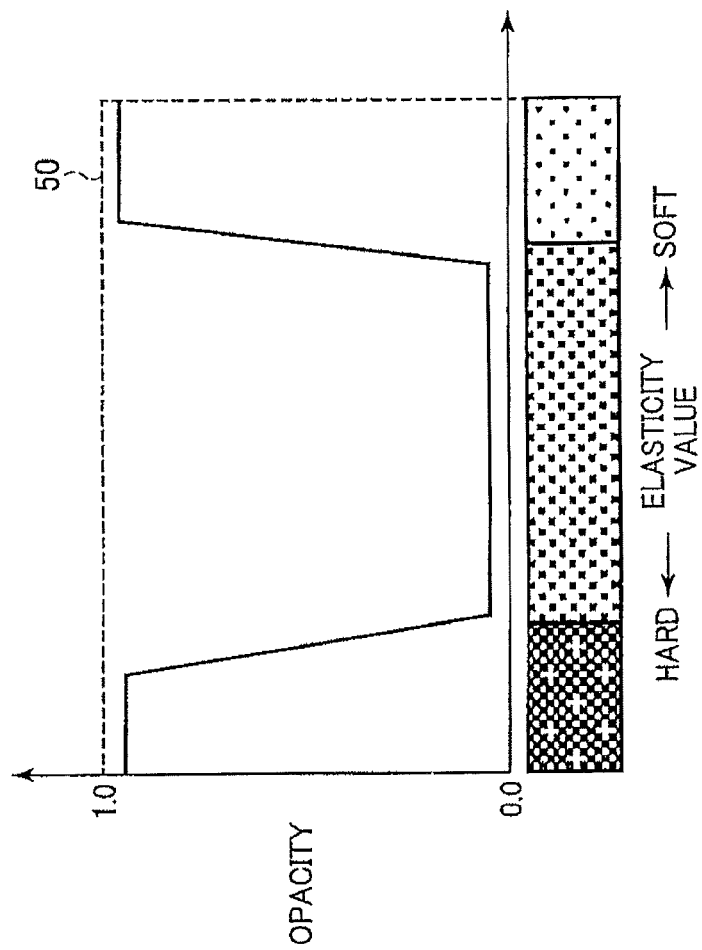
FIG. 5 is a diagram depicting an elasticity opacity according to the elasticity value.

FIG. 5 is a diagram depicting the elasticity opacity according to the elasticity value. The three-dimensional elasticity image constructing section 17 performs the volume rendering using the elasticity opacity according to the elasticity value. The elasticity opacity table creating section (elasticity opacity setting section) 16 associates the elasticity value with the elasticity opacity to set the elasticity opacity according to the elasticity value.

As depicted in FIG. 5, the elasticity opacity table creating section (elasticity opacity setting section) 16 creates an elasticity opacity table 50 in which the axis of abscissas represents the elasticity value for the elasticity volume data and in which the axis of ordinate represents the opacity. The three-dimensional elasticity image constructing section 17 uses the opacity set in the elasticity opacity table 50 as the elasticity opacity. As depicted in FIG. 5, the elasticity opacity table creating section (elasticity opacity setting section) 16 sets high elasticity opacities for a hard site (for example, a site with an elasticity value smaller than a predetermined reference value) and a soft site (for example, a site with an elasticity value larger than the predetermined reference value) that are likely to be sites of interest, and sets a low elasticity opacity for a site with an intermediate hardness which is unlikely to be a site of interest. However, the elasticity opacity table creating section (elasticity opacity setting section) 16 may set a low elasticity opacity for a hard site or a soft site depending on intended use (for example, the hardness of the site of interest). In other words, the elasticity opacity table creating section (elasticity opacity setting section) 16 may associate an elasticity opacity smaller than the elasticity opacity associated with the elasticity value of the site of interest, with a site other than the site of interest (for example, the site with the intermediate hardness).

The small value of the elasticity opacity depends on the number of voxels in a line-of-sight direction in the volume rendering. However, in general, setting a value of smaller than "0.1" results in construction of a three-dimensional elasticity image in which the site other than the site of interest is translucent. However, given that the site other than the site of interest is constructed using a translucent three-dimensional elasticity image, the value of the elasticity opacity may be equal to or larger than "0.1". The large value of the elasticity opacity depends on the number of voxels in a line-of-sight direction in the volume rendering. However, in general, setting a value of at least "0.5" results in construction of a three-dimensional elasticity image in which the site of interest is opaque. However, given that the site of interest is constructed using an opaque three-dimensional elasticity image, the value of the elasticity opacity may be smaller than "0.5".

Figure 6:
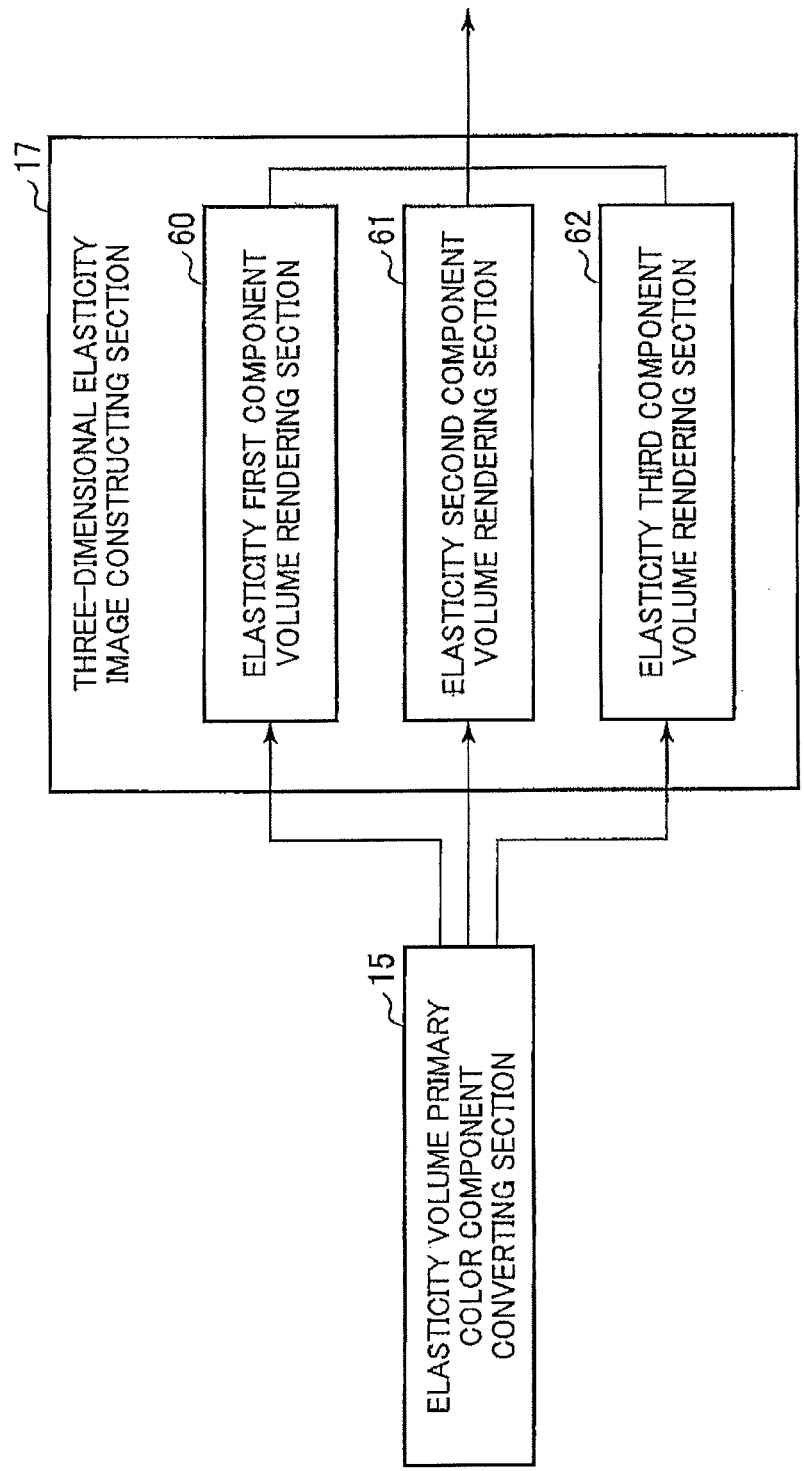
FIG. 6 is a diagram depicting an example of a three-dimensional elasticity image constructing section.

FIG. 6 is a diagram depicting an example of the three-dimensional elasticity image constructing section 17. As depicted in FIG. 6, the three-dimensional elasticity image constructing section 17 includes an elasticity first component volume rendering section 60, an elasticity second component volume rendering section 61, and an elasticity third component volume rendering section 62. The elasticity first component volume rendering section 60 performs the volume rendering with shading on the elasticity first component volume data. The elasticity second component volume rendering section 61 performs the volume rendering with shading on the elasticity second component volume data. The elasticity third component volume rendering section 62 performs the volume rendering with shading on the elasticity third component volume data.

The volume rendering with shading is performed using Expressions (4) to (6). The three-dimensional elasticity image constructing section 17 creates a three-dimensional elasticity image by combining (synthesizing) the results of the volume rendering with shading performed on the volume data on each of the components (for example, RGB components).

$$Cout(i) = Cout(i-1) + (1 - Aout(i-1)) \cdot A(i) \cdot C(i) \cdot S(i) \quad (4)$$

$$Aout(i) = Aout(i-1) + (1 - Aout(i-1)) \cdot A(i) \quad (5)$$

$$A(i) = \text{Opacity}[E(i)] \quad (6)$$

C(i) designates a component value of the "i"th voxel on the line of sight when a three-dimensional elasticity image is viewed at a predetermined point on a two-dimensional plane of projection (three-dimensional elasticity image) to be created. In the present embodiment, C(i) is the value of each primary color component (for example, each of RGB primary color component values) in a voxel. Cout(i) designates an output pixel value. For example, when N voxels are arranged on the line of sight, Cout(N−1) designates a primary color component value resulting from integration of the primary color component values "C(i=0)" to "C(i=N−1)". Cout(N−1) is a finally output pixel value. Cout(i−1) designates a component value (primary color component value) resulting from integration of the values up to the "i−1"th value.

E(i) designates the "i"th elasticity value on the line of sight when the three-dimensional elasticity image is viewed at the predetermined point on the two-dimensional plane of projection (three-dimensional elasticity image) to be created. A(i) designates the opacity (elasticity opacity) according to the "i"th elasticity value E(i) on the line of the sight, and is set in the elasticity opacity table 50 with a value ranging from "0" to "1.0" as depicted in FIG. 5. The elasticity opacity determines the rate of contribution to the output two-dimensional plane of projection (three-dimensional elasticity image). Aout(i−1) designates the opacity (elasticity opacity) integrated each time the voxel is passed through, and is an integral value of the opacities (elasticity opacities) up to the "i−1"th opacity.

S(i) designates a shading weight component for the shading determined by the gradient calculated from the elasticity value E(i) and peripheral elasticity values. For example, when the direction of a light beam from the light source aligns with the normal direction in the plane around the voxel "i", the light beam is most significantly reflected, and thus, the shading weight component "S(i)=1.0" is provided.

When the direction of the light source is orthogonal to the normal direction, the light beam is most insignificantly reflected, and thus, the shading weight component "S(i)=0.0" is provided. Thus, the shading weight component S(i) exhibits a shading effect.

Both Cout(i) and Aout(i) have an initial value of "0". As illustrated in Expression (5), Aout(i) is integrated each time the voxel is passed through, and converges to "1.0". Hence, as illustrated in Expression (4), when the integral value of the opacities up to the "i−1"th opacity is "1.0" (Aout(i−1)≈1.0), the "i"th and subsequent component values C(i) are not reflected in the output image.

As described above, the three-dimensional elasticity image constructing section 17 performs the volume rendering with shading on at least one of the plurality of primary color components to construct a three-dimensional elasticity image. In the present embodiment, the elasticity volume primary color component converting section 15 separates (converts) the elasticity volume data into the three primary color components for color image display, performs the volume rendering with shading on each of the primary color components, and combines (synthesizes) each of the primary color components together. The elasticity volume primary color component converting section 15 can thus obtain a three-dimensional elasticity image with hue information held.

For example, when the primary color component value "C(i)" for the voxel corresponding to blue is R=50, G=50, and B=255 and the value of "(1−Aout(i−1)) A(i)·S(i)" of Expression (4) is "0.5", the value "(1−Aout(i−1))·A(i)·C(i)·S(i)" to be added to "Cout(i−1)" in Expression (4) for each primary color component value is R=25, G=25, and B=127. In this case, the color expressed by R=25, G=25, and B=127 is a livid color which has a hue remaining on the blue side but which has a reduced luminosity. As described above, the three-dimensional elasticity image subjected to the volume rendering with shading is a stereoscopic image which maintains the hue and in which sites to which the elasticity opacity "A(i)" and the shading weight component "S(i)" for shading make a major contribution have a reduced luminosity.

Figure 7:
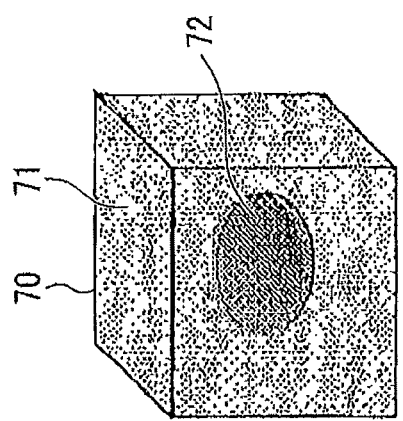
FIG. 7 is a diagram depicting an example of a three-dimensional elasticity image on which volume rendering with shading has been performed.

FIG. 7 is a diagram depicting an example of a three-dimensional elasticity image subjected to the volume rendering with shading. As depicted in FIG. 7, a three-dimensional elasticity image 70 has a hard volume (site of interest) in a volume with the intermediate hardness (site other than the site of interest). The volume with the intermediate hardness is displayed by a three-dimensional elasticity image 71, and the hard volume is displayed by a three-dimensional elasticity image 72. For the elasticity opacity table 50 in FIG. 5, the elasticity opacity table creating section (elasticity opacity setting section) 16 sets, for the site other than the site of interest (volume with the intermediate hardness), an elasticity opacity smaller than an elasticity opacity set for the elasticity value for the site of interest (hard volume). Thus, the three-dimensional elasticity image 70 is constructed in which the three-dimensional elasticity image 71 corresponding to the volume with the intermediate hardness is translucent and which allows the three-dimensional elasticity image 72 corresponding to the hard volume to be determined to be present inside the translucent three-dimensional elasticity image 71.

However, even when the site other than the site of interest (three-dimensional elasticity image 71) is displayed in a translucent manner by setting a low opacity, the shading is performed on the translucent site (site other than the site of interest), possibly making the three-dimensional elasticity image 70 visually bad. For example, the shading weight component for shading also contributes to the three-dimensional elasticity image 71 corresponding to the volume with the intermediate hardness, leading to display of a visually bad three-dimensional elasticity image 71 with dark green extracted in a patchy fashion. Furthermore, the shading is performed also on the translucent site (site other than the site of interest) and thus darkens site other than the site of interest, preventing the site of interest from being clearly displayed.

Thus, the ultrasound diagnostic apparatus 200 in the present embodiment includes the three-dimensional elasticity image constructing section 17 that performs the volume rendering with shading on the elasticity volume data with the elasticity value to construct a three-dimensional elasticity image. The three-dimensional elasticity image constructing section 17 disables the shading for a portion with at least one of a predetermined elasticity opacity according to the elasticity value and a predetermined elasticity value.

In the present embodiment, the elasticity first component volume rendering section 60, elasticity second component volume rendering section 61, and elasticity third component volume rendering section 62 in FIG. 6 use the shading weight component S(i) set to "1.0" to perform the volume rendering with shading on a voxel for which an elasticity opacity smaller than a predetermined threshold (reference value) is set, thus disabling the shading. Setting the shading weight component S(i) to "1.0" allows production of effects similar to the effects of a case where the light beam is most significantly reflected, enabling the shading to be disabled.

Any threshold (reference value) Ath for the elasticity opacity is preset, and in Expression (4), the three-dimensional elasticity image constructing section 17 performs the volume rendering based on the threshold (reference value) Ath and disables the shading. For example, for "A(i)≤Ath", the shading weight component S(i) is changed to "S(i)=1.0" to disable the shading. On the other hand, for "A(i)>Ath", "S(i)=S(i)" is set and the shading weight component S(i) is unchanged to enable the shading.

Figure 8:
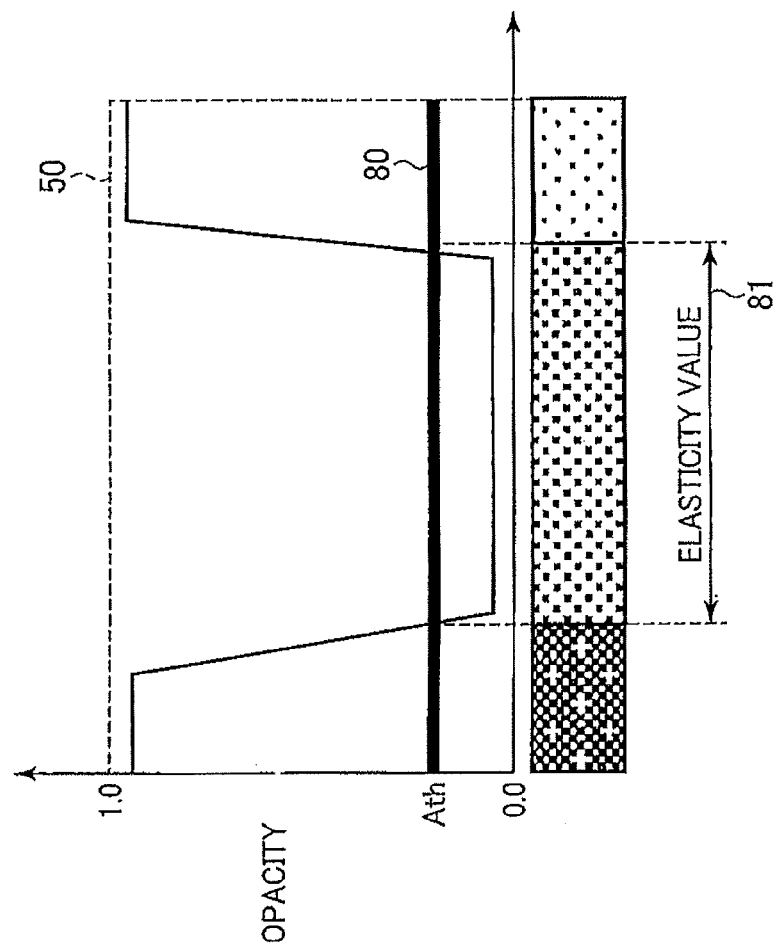
FIG. 8 is a diagram depicting any threshold (reference value) for the elasticity opacity.

FIG. 8 is a diagram depicting any threshold (reference value) for the elasticity opacity. As depicted in FIG. 8, the threshold (reference value) Ath is preset and indicated as a line 80 in the elasticity opacity table 50 in FIG. 5. The threshold (reference value) Ath is set larger than the elasticity opacity associated with the site other than the site of interest (for example, a range 81 of the elasticity value for the intermediate hardness). For the voxel included in the site other than the site of interest (elasticity value range 81) to which an elasticity opacity equal to or smaller than the threshold (reference value) Ath is assigned, "A(i)≤Ath", and thus, setting the threshold (reference value) Ath changes the shading weight component S(i) to "S(i)=1.0". Then, the volume rendering is performed with the shading disabled. Hence, the effect of the shading is disabled for the translucent site. As described above, the three-dimensional elasticity image constructing section 17 disables the shading when the elasticity opacity is smaller than the preset reference value. The three-dimensional elasticity image constructing section 17 disables the shading of the portion with at least one of a predetermined elasticity opacity according to the elasticity value and a predetermined elasticity value.

Figure 9:
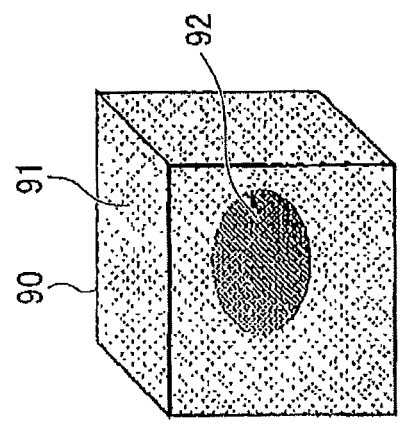
FIG. 9 is a diagram depicting an example of a three-dimensional elasticity image for which the shading is disabled by a three-dimensional elasticity image constructing section.

FIG. 9 is a diagram depicting an example of a three-dimensional elasticity image for which the shading is disabled by the three-dimensional elasticity image constructing section 17. As depicted in FIG. 9, a three-dimensional elasticity image 90 has a hard volume (site of interest) in a volume with the intermediate hardness (site other than the site of interest). In the three-dimensional elasticity image 90, the volume with the intermediate hardness is displayed by a three-dimensional elasticity image 91, and the hard volume is displayed by a three-dimensional elasticity image 92.

For the elasticity opacity table 50 in FIG. 5 and FIG. 8, the elasticity opacity table creating section (elasticity opacity setting section) 16 sets, for the site other than the site of interest (intermediate hardness volume), an elasticity opacity smaller than the elasticity opacity set for the elasticity value for the site of interest (hard volume). Thus, the three-dimensional elasticity image 90 is constructed in which the three-dimensional elasticity image 91 corresponding to the volume with the intermediate hardness is translucent and which allows the three-dimensional elasticity image 92 corresponding to the hard volume to be determined to be present inside the translucent three-dimensional elasticity image 91.

Unlike in the three-dimensional elasticity image 70 in FIG. 7, in the three-dimensional elasticity image 90, the shading is disabled for the three-dimensional elasticity image 91 corresponding to the volume with the intermediate hardness. In FIG. 9, an elasticity opacity equal to or smaller than the threshold (reference value) Ath in FIG. 8 is assigned to the three-dimensional elasticity image 91 corresponding to the volume with the intermediate hardness, and is smaller than the preset reference value. Thus, the three-dimensional elasticity image constructing section 17 disables the shading for the site other than the site of interest (three-dimensional elasticity image 91).

An elasticity opacity smaller than the elasticity opacity associated with the elasticity value for the site of interest is associated with the site other than the site of interest, and the elasticity opacity of the site other than the site of interest is set smaller than the elasticity opacity of the site of interest. Thus, the site other than the site of interest (three-dimensional elasticity image 91) is displayed in a translucent manner, and the effect of the shading is disabled for the site other than the site of interest (three-dimensional elasticity image 91). Then, a site other than the site of interest (three-dimensional elasticity image 91) is extracted which is uniform and visually good and which has the intermediate hardness.

On the other hand, an elasticity opacity exceeding the threshold (reference value) Ath in FIG. 8 is assigned to the three-dimensional elasticity image 92 corresponding to the hard site (site of interest), and is larger than the preset reference value. Thus, the three-dimensional elasticity image constructing section 17 enables the shading for the site of interest (three-dimensional elasticity image 92).

An elasticity opacity smaller than the elasticity opacity associated with the elasticity value for the site of interest is associated with the site other than the site of interest, and the opacity of the site of interest is set larger than the opacity of the site other than the site of interest. Thus, the effect of the shading is enabled for the site of interest (three-dimensional elasticity image 92), allowing a stereoscopic and hard three-dimensional elasticity image 92 to be shaded and extracted.

As described above, the ultrasound diagnostic apparatus 200 in the present embodiment includes the elasticity volume primary color component converting section 15 that converts the elasticity volume data into a plurality of primary color components. The three-dimensional elasticity image constructing section 17 performs the volume rendering with shading on at least one of the plurality of primary color components to construct a three-dimensional elasticity image. The three-dimensional elasticity image constructing section 17 disables the shading of at least one of the plurality of primary color components for the portion with at least one of a predetermined elasticity opacity according to the elasticity value and the elasticity value of a predetermined value.

As described above, the present embodiment allows construction of a stereoscopic three-dimensional elasticity image for which the shading is enabled, for the site of interest with a high elasticity opacity, and construction of a visually good, translucent three-dimensional elasticity image for which the shading is disabled, for the site other than the site of interest with a low elasticity opacity. As a result, the site of interest can be constructed as a noticeable three-dimensional elasticity image.

In the present embodiment, the elasticity volume primary color component converting section 15 separates (converts) the elasticity volume data into the three primary color components for color image display. However, any other method may be used. For example, in separating (converting), based on the elasticity value, the elasticity volume data into volume data with a hard elasticity value (elasticity value component corresponding to the site of interest), volume data with an elasticity value for the intermediate hardness (elasticity value component corresponding to the site other than the site of interest), and volume data with a soft elasticity value (elasticity value component corresponding to the site of interest) and performing the volume rendering on each of the volume data, the three-dimensional elasticity image constructing section 17 sets an opacity smaller than the opacity of the volume data with the hard elasticity value and the volume data with the soft elasticity value (elasticity value components corresponding to the sites of interest), for the volume data with the elasticity value for the intermediate hardness (elasticity value component corresponding to the site other than the site of interest) and applying the present embodiment to allow production of effects similar to the above-described effects.

In other words, the ultrasound diagnostic apparatus 200 includes the sending section 3 that sends an ultrasonic wave to the diagnosing object 1 via the ultrasound probe 2, the receiving section 4 that receives the reflected echo signal from the diagnosing object 1, the three-dimensional elasticity image constructing section 17 that performs the volume rendering with shading on the elasticity volume data with the elasticity value based on the reflected echo signal to construct a three-dimensional elasticity image, and the image display section that displays the three-dimensional elasticity image. The three-dimensional elasticity image constructing section 17 separates (converts) the elasticity volume data into a plurality of elasticity value components based on the elasticity value and performs the volume rendering with shading on the plurality of elasticity value components to construct a three-dimensional synthetic image. The three-dimensional elasticity image constructing section 17 disables the shading of at least one of the plurality of elasticity value components.

Furthermore, in the present embodiment, "S(i)=1.0" is set in Expression (4) to disable the shading. However, S(i) may be set to a relatively large value smaller than "1.0" as long as the effect that disables the shading can be achieved to allow a visually good three-dimensional image to be constructed.

Second Embodiment

Figure 10:
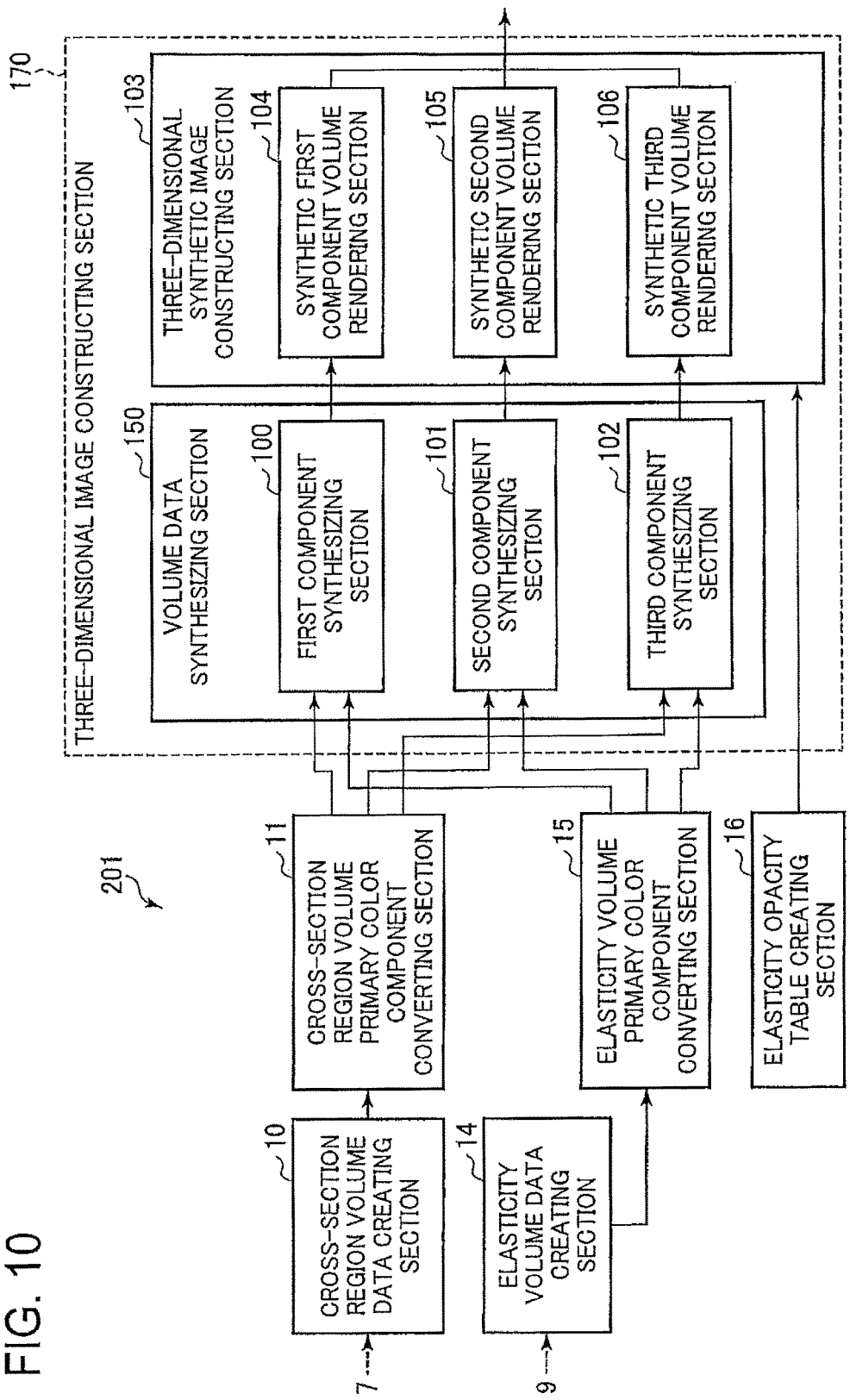
FIG. 10 is a diagram depicting an example of an ultrasound diagnostic apparatus according to a second embodiment.

An ultrasound diagnostic apparatus according to an embodiment of the present invention will be described using the drawings. Mainly differences from the first embodiment will be described, and other elements are similar to the corresponding elements in the first embodiment. FIG. 10 is a diagram depicting an example of the ultrasound diagnostic apparatus in the present embodiment. As depicted in FIG. 10, a three-dimensional image constructing section 170 includes a volume data synthesizing section 150, and a three-dimensional synthetic image constructing section 103. In perform volume rendering with shading on volume data, the three-dimensional image constructing section 170 disables the shading of a portion with at least one of a predetermined elasticity opacity according to an elasticity value and a predetermined elasticity value to construct a three-dimensional image.

A feature of an ultrasound diagnostic apparatus 201 in the present embodiment is such that the ultrasound diagnostic apparatus 201 includes a sending section 3 that sends an ultrasonic wave to a diagnosing object 1 via an ultrasound probe 2, a receiving section 4 that receives a reflected echo signal from the diagnosing object 1, a cross-section region volume data creating section 10 that creates cross-section region volume data with a cross-section region image of the diagnosing object 1 based on the reflected echo signal, a elasticity volume data creating section 14 that creates elasticity volume data with an elasticity value based on the reflected echo signal, a volume data synthesizing section 150 that synthesizes the cross-section region volume data and the elasticity volume data to create synthetic volume data, a three-dimensional synthetic image constructing section 103 that perform the volume rendering with shading on the synthetic volume data to construct a three-dimensional synthetic image, and an image display section 19 that displays the three-dimensional synthetic image, and such that the three-dimensional synthetic image constructing section 103 disables the shading of a portion with at least one of a predetermined cross-section region opacity according to a luminance of the cross-section region volume data, a predetermined elasticity opacity according to the elasticity value, and the elasticity value of a predetermined value.

Furthermore, another feature of the ultrasound diagnostic apparatus 201 in the present embodiment is that the ultrasound diagnostic apparatus 201 includes a cross-section region volume primary color component converting section 11 that converts the cross-section region volume data into a plurality of primary color components, and a elasticity volume primary color component converting section 15 that converts the elasticity volume data into a plurality of primary color components, and such that the volume data synthesizing section 150 synthesizes the cross-section region volume data and the elasticity volume data according to the plurality of primary color components to create a plurality of the synthetic volume data according to the plurality of primary color components, and the three-dimensional synthetic image constructing section 103 performs the volume rendering with shading on at least one of the plurality of synthetic volume data to construct a three-dimensional synthetic image and disables the shading of at least one of the plurality of synthetic volume data for a portion with at least one of a predetermined elasticity opacity according to the elasticity value and the elasticity value of a predetermined value.

The cross-section region volume primary color component converting section 11 separates (converts) the cross-section region volume data into three primary color components for color image display corresponding to a luminance value, and the elasticity volume primary color component converting section 15 separates (converts) the elasticity volume data into three primary color components for color image display corresponding to the elasticity value.

After the cross-section region volume primary color component converting section 11 and the elasticity volume primary color component converting section 15 separate (convert) the cross-section region volume data and the elasticity volume data into the three primary color components for color image display, the three-dimensional image constructing section 170 synthesizes the cross-section region volume data and the elasticity volume data for each component (for example, RGB components) and performs the volume rendering on the synthetic volume data on each component using the elasticity opacity.

In FIG. 10, the components preceding the cross-section region volume data creating section 10 and the elasticity volume data creating section 14 (three-dimensional image constructing section 170) are similar to the corresponding components in the first embodiment and are thus omitted. Furthermore, the components succeeding the three-dimensional synthetic image constructing section 103 (three-dimensional image constructing section 170) are also similar to the corresponding components in the first embodiment and are thus omitted.

In the present embodiment, a case will be described where the cross-section region volume primary color component converting section 11 and the elasticity volume primary color component converting section 15 separates (converts) the volume data into the three primary colors, R (Red), G (Green), and B (Blue), as in the first embodiment. Of course, instead of these components, the cross-section region volume primary color component converting section 11 and the elasticity volume primary color component converting section 15 may separate (convert) the volume data into other primary color components.

The volume data synthesizing section 150 includes a first component synthesizing section 100, a second component synthesizing section 101, and a third component synthesizing section 102. The first component synthesizing section 100, the second component synthesizing section 101, and the third component synthesizing section 102 synthesize the cross-section region volume data and the elasticity volume data for each of the three primary color components for color image display (for example, the RGB components).

For example, the three-dimensional synthetic image constructing section 103 uses the first component synthesizing section 100 to synthesize R component volume data resulting from separation (conversion) from the cross-section region volume data and R component volume data resulting from separation (conversion) from the elasticity volume data.

The R component volume data resulting from separation from the cross-section region volume data is hereinafter referred to as cross-section region volume data R1, R component volume data resulting from separation from the elasticity volume data is hereinafter referred to as elasticity volume data R2, and R component volume data resulting from synthesis of the cross-section region volume data R1 and the elasticity volume data R2 is hereinafter referred to as synthetic volume data R3, the first component synthesizing section 100 performs synthesis using following Expression (7).

$$R3 = (1-\alpha) \times R1 + \alpha \times R2 \quad (7)$$

α designates a synthesis weight coefficient of "0 to 1.0" that is set via the operation section 20.

As is the case with the R component, the second component synthesizing section 101 synthesizes cross-section region volume data G1 and elasticity volume data G2 to create synthetic volume data G3, and the third component synthesizing section 102 synthesizes cross-section region volume data B1 and elasticity volume data B2 to create synthetic volume data B3.

The three-dimensional synthetic image constructing section 103 includes a synthetic first component volume rendering section 104, a synthetic second component volume rendering section 105, and a synthetic third component volume rendering section 106.

The synthetic first component volume rendering section 104 performs the volume rendering on the synthetic volume data R3. The synthetic second component volume rendering section 105 performs the volume rendering on the synthetic volume data G3. The synthetic third component volume rendering section 106 performs the volume rendering on the synthetic volume data B3.

In the present embodiment, the three-dimensional synthetic image constructing section 103 performs the volume rendering in accordance with Expressions (4) to (6) illustrated above and uses the elasticity opacity as the opacity. Furthermore, the three-dimensional synthetic image constructing section 103 may use, as S(i) in Expression (4), a predetermined shading weight component according to the luminance of the cross-section region volume data or a shading weight component according to the elasticity value for the elasticity volume data.

In the present embodiment, an elasticity opacity table creating section (elasticity opacity setting section) 16 creates an elasticity opacity table 50 and sets a threshold (reference value) Ath as a line 80 as depicted in FIG. 5 and FIG. 8. Furthermore, as is the case with the first embodiment, the threshold (reference value) Ath is set to be larger than the elasticity opacity associated with a site other than a site of interest (for example, a range 81 of the elasticity value for an intermediate hardness). For a voxel included in the site other than the site of interest (elasticity value range 81) to which an elasticity opacity equal to or smaller than the threshold (reference value) Ath is assigned, "A(i)≤Ath". Thus, the shading weight component S(i) is changed to "S(i)=1.0", and the volume rendering is performed with the shading disabled.

Figure 11:
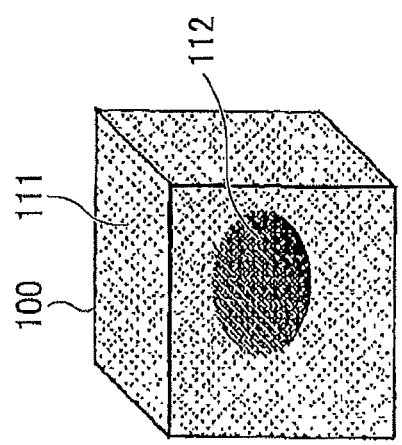
FIG. 11 is a diagram depicting an example of three-dimensional synthetic image for which the shading is disabled by a three-dimensional synthetic image constructing section.

FIG. 11 is a diagram depicting an example of a three-dimensional synthetic image for which the shading is disabled by the three-dimensional synthetic image constructing section 103. As depicted in FIG. 11, a three-dimensional synthetic image 110 has a hard volume (site of interest) in a volume with an intermediate hardness (site other than the site of interest). In the three-dimensional synthetic image 110, the volume with the intermediate hardness is displayed by a three-dimensional synthetic image 111, and the hard volume is displayed by a three-dimensional synthetic image 112.

Unlike in the first embodiment, the cross-section region volume data and the elasticity volume data are synthesized. Thus, in the three-dimensional synthetic image 110, information on a cross-section region image is added to information on an elasticity image. The cross-section region image mainly reflects biological tissue information, and thus, the three-dimensional synthetic image 110 reflects the tissue information and the elasticity information. Consequently, a tissue state and an elasticity state can be simultaneously checked.

For example, a tumor mainly exhibits low echo intensity and is often extracted in black in a cross-section region image. Furthermore, the tumor is often harder than peripheral tissues and is thus often extracted in blue in an elasticity image. Therefore, when the tumor site (site of interest) is constructed as a three-dimensional synthetic image, a dark blue, stereoscopic synthetic image is constructed in which the black color of the cross-section region image and the blue color of the elasticity image are synthesized. A normal tissue such as fat is often extracted mainly in gray or white in a cross-section region image. Furthermore, the normal tissue such as the fat often has the intermediate hardness, and is often extracted mainly in green in an elasticity image. Therefore, when the normal tissue such as the fat (site other than the site of interest) is constructed as a three-dimensional synthetic image, a bright green, stereoscopic synthetic image is constructed in which the gray or white color of the cross-section region image and the green color of the elasticity image are synthesized. As described above, the tissue state and the elasticity state can be simultaneously checked based on the hue.

According to the present embodiment, the normal tissue with the intermediate hardness (site other than the site of interest) is extracted as the three-dimensional synthetic image 111 with the intermediate hardness. As depicted in FIG. 5 and FIG. 8, a low elasticity opacity is set for the normal tissue with the intermediate hardness (site other than the site of interest). Thus, the three-dimensional synthetic image 111 with the intermediate hardness is translucent, allowing identification of the hard three-dimensional synthetic image 112 (site of interest) present inside the three-dimensional synthetic image 111 with the intermediate hardness. Furthermore, for the site with the intermediate hardness, the elasticity opacity is set smaller than the threshold (reference value) Ath to disable the effect of the shading, allowing a uniform and visually good three-dimensional synthetic image 111 with the intermediate hardness to be constructed, as depicted in FIG. 8. Moreover, the hard site (site of interest) suspected to be an abnormal tissue such as a tumor can be constructed as the hard three-dimensional synthetic image 112. For the hard three-dimensional synthetic image 112, the elasticity opacity is set larger than the threshold (reference value) Ath to enable the effect of the shading, allowing construction of a stereoscopic, hard three-dimensional synthetic image 112 reflecting the tissue state and the elasticity state.

As described above, according to the present embodiment, the cross-section region volume data and the elasticity volume data are synthesized such that, for the site of interest with a high elasticity opacity, the shading is enabled to construct a stereoscopic three-dimensional synthetic image that allows the tissue information and the elasticity information to be checked at a first glance and such that, for the site other than the site of interest with a low elasticity opacity, the shading is disabled to allow construction of a visually good and translucent three-dimensional synthetic image. As a result, the tissue state and elasticity state of the site of interest enable the site of interest to be constructed as a noticeable three-dimensional synthetic image.

The embodiments according to the present invention have been described. However, the present invention is not limited to these embodiments. The embodiments may be changed or varied within the scope recited in the claims.

Figure 12:
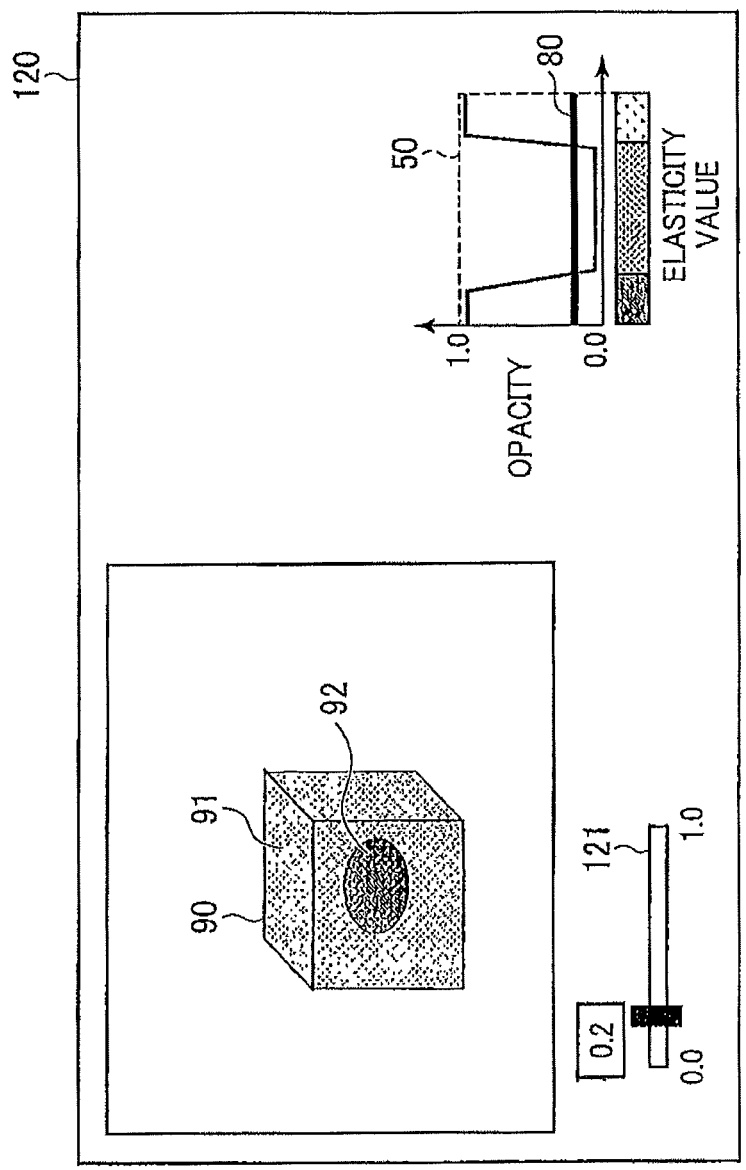
FIG. 12 is a diagram depicting a display example of an image display section.

For example, the operation section 20 may adjust the threshold (reference value) Ath. FIG. 12 is a diagram depicting a display example of the image display section 19. In a screen 120 of the image display section 19, the elasticity opacity table 50 in FIG. 8 and a three-dimensional elasticity image 90 in FIG. 9 are displayed. Furthermore, an elasticity opacity threshold setting section 121 is displayed. The elasticity opacity threshold setting section 121 allows the threshold (reference value) Ath to be adjusted (set) using a numerical value setting section or a slide bar corresponding to the operation section 20. In FIG. 12, "threshold (reference value) Ath=0.2" is set. In this manner, the operation section 20 may adjust the threshold (reference value) Ath to adjust the site for which the shading is disabled (site other than the site of interest).

Figure 13:
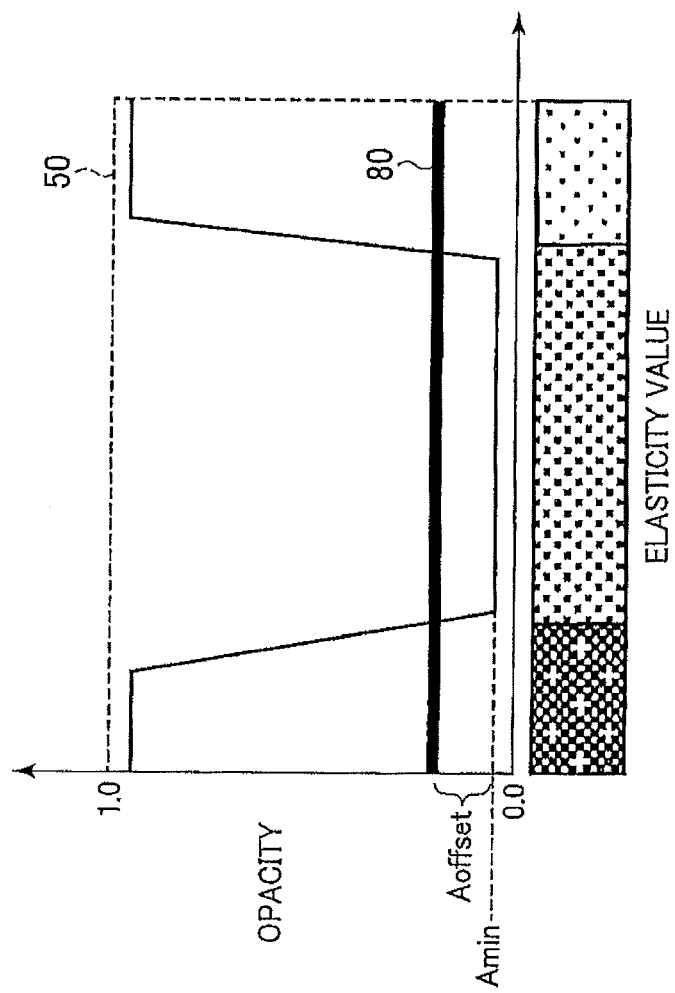
FIG. 13 is a diagram depicting a threshold (reference value) set based on a minimum value of the elasticity opacity in an elasticity opacity table.

Furthermore, the threshold (reference value) Ath may be set based on the minimum value of the elasticity opacity according to the elasticity value. FIG. 13 is a diagram depicting the elasticity opacity table 50 indicating the threshold (reference value) Ath set based on the minimum value of the elasticity opacity. As depicted in FIG. 13, the elasticity opacity table 50 created by the elasticity opacity table creating section (elasticity opacity setting section) 16 indicates a line 80 corresponding to the threshold (reference value) Ath. In the elasticity opacity table 50, the minimum value of the elasticity opacity is "Amin".

When the threshold (reference value) Ath is set based on the minimum value of the elasticity opacity according to the elasticity value, the threshold (reference value) Ath may be a value adding any value Aoffset to the minimum value Amin of the elasticity opacity. In this case, the threshold (reference value) Ath is expressed by Expression (8) illustrated below. Aoffset is any constant.

$$Ath = Amin + Aoffset \quad (8)$$

Furthermore, when the threshold (reference value) Ath is set based on the minimum value of the elasticity opacity according to the elasticity value, the threshold (reference value) Ath may be a value multiplying the minimum value of the elasticity opacity by any weight component. In this case, the threshold (reference value) Ath is expressed by Expression (9) illustrated below. The weight component Acoeff is any constant larger than "1".

$$Ath = Amin \cdot A\,coeff \quad (9)$$

As a result, the threshold (reference value) Ath for the elasticity opacity is automatically set, eliminating the need for a user to manually set the threshold (reference value) Ath to facilitate setting of the threshold (reference value) Ath. An opacity of "0" represents a complete transparent area and may be used for a special purpose such as removal of noise, and thus, "Amin" may be the minimum value other than an elasticity opacity of "0".

Figure 14:
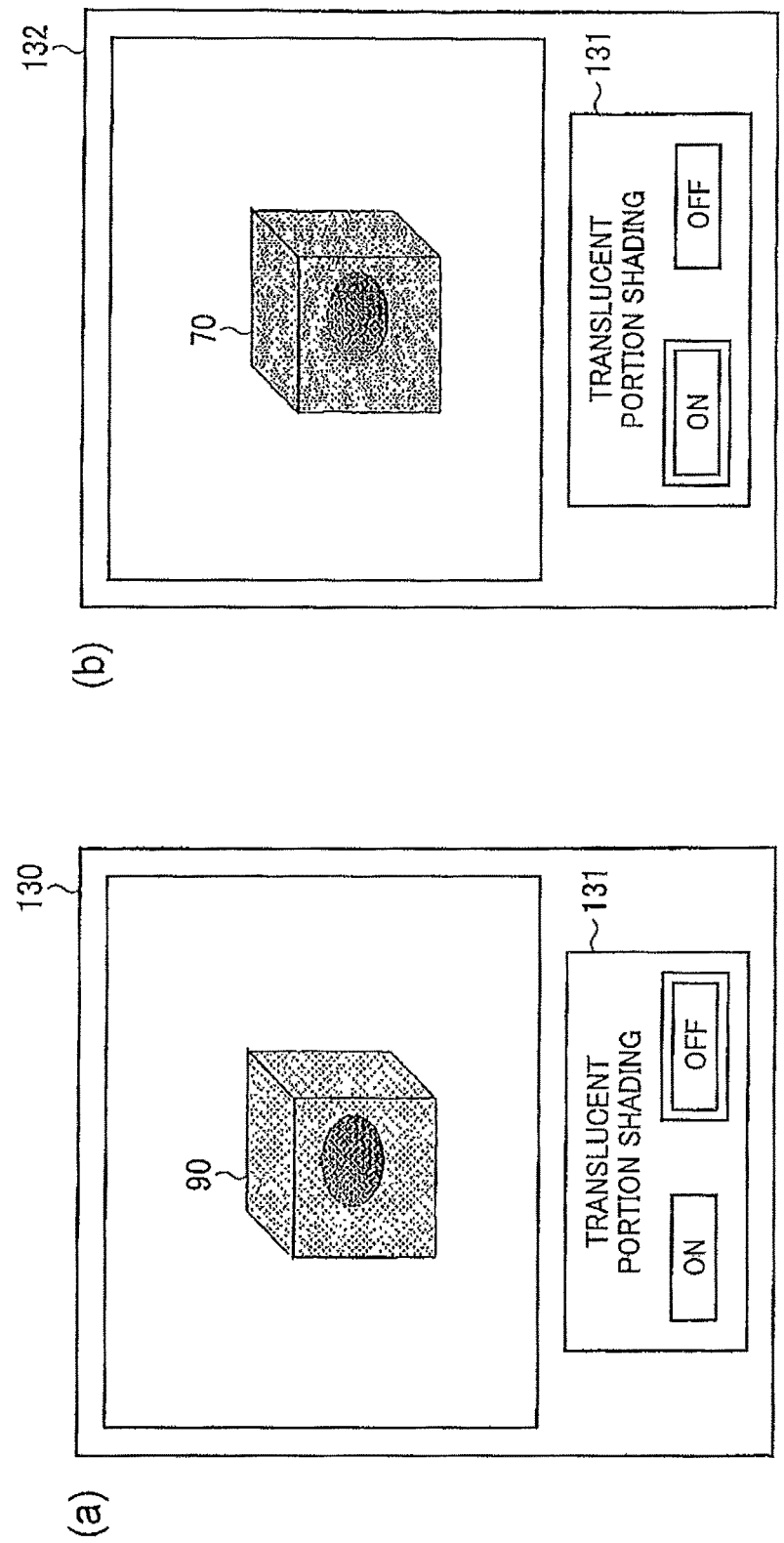
FIG. 14 is a diagram depicting an example where a three-dimensional elasticity image for which the shading is disabled and a three-dimensional elasticity image for which the shading is enabled are displayed in a switching manner.

Furthermore, the image display section 19 may switchably display both or one of the three-dimensional elasticity image for which the shading is disabled and the three-dimensional elasticity image for which the shading is enabled. In this case, the operation section 20 sets whether or not to disable the shading of a site (site other than the site of interest) for which an elasticity opacity smaller than the threshold (reference value) Ath for the elasticity opacity is set. Then, the control section 21 switches to both or one of the three-dimensional elasticity image for which the shading is disabled and the three-dimensional elasticity image for which the shading is enabled. FIG. 14 is a diagram illustrating an example where the three-dimensional elasticity image for which the shading is disabled and the three-dimensional elasticity image for which the shading is enabled are switchably displayed. A screen 130 of the image display section 19 displays the three-dimensional elasticity image 90 for which the shading is disabled. A screen 132 of the image display section 19 displays a three-dimensional elasticity image 70 for which the shading is enabled.

Furthermore, the images 130 and 132 display a shading control section 131. The shading control section 131 allows whether to enable or disable the shading of a site with a low elasticity opacity (site other than the site of interest) to be set using a button corresponding to the operation section 20.

FIG. 14(a) depicts a state where the shading control section 131 turns off (in other words, disables) the shading of the site with a low elasticity opacity (site other than the site of interest) FIG. 14(b) depicts a state where the shading control section 131 turns on (in other words, enables) the shading of the site with a low elasticity opacity (site other than the site of interest). The user switches on and off the shading using the shading control section 131 via the operation section 20. As described above, enabling or disabling the shading can be freely selected.

Furthermore, the elasticity opacity table creating section (elasticity opacity setting section) 16 associates an elasticity opacity smaller than the elasticity opacity associated with the elasticity value for the site of interest, with the site other than the site of interest. The three-dimensional elasticity image constructing section 17 may disable the shading of the site other than the site of interest based on the elasticity value or the elasticity opacity. The elasticity opacity table creating section (elasticity opacity setting section) 16 sets the elasticity opacity used for the volume rendering to be smaller than the elasticity opacity of the site of interest for the site other than the site of interest determined based on the elasticity value. The three-dimensional elasticity image constructing section 17 disable the shading in the volume rendering for the site other than the site of interest.

Figure 15:
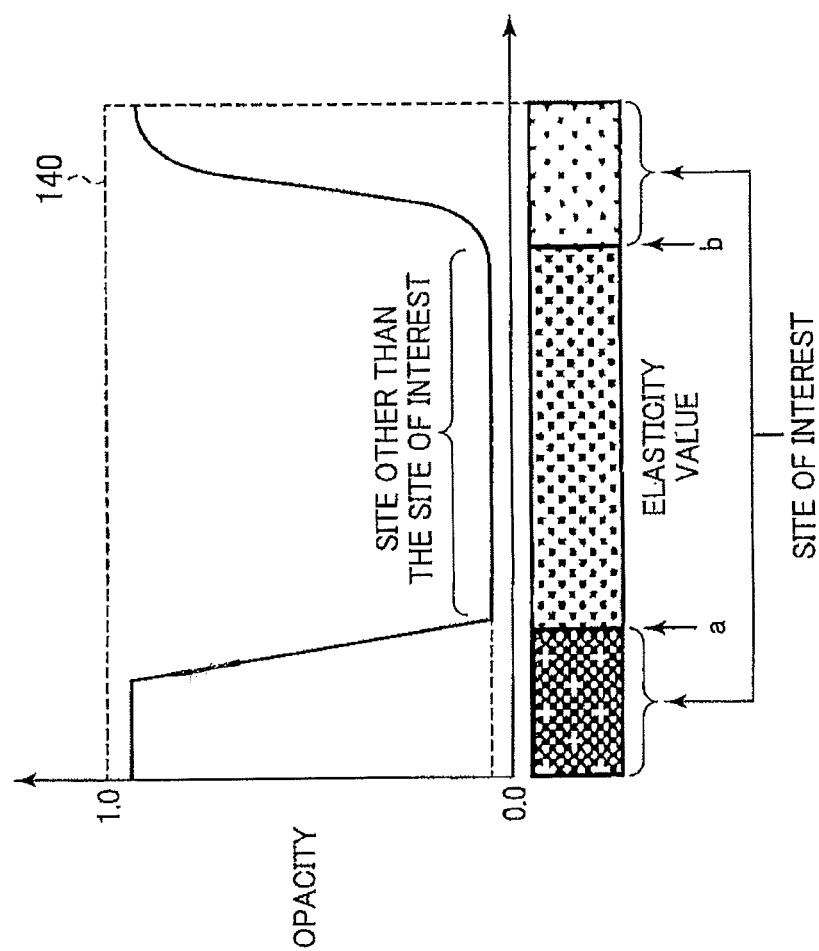
FIG. 15 is a diagram depicting the elasticity opacity of a site of interest and a site other than the site of interest.

FIG. 15 is a diagram depicting the elasticity opacities of the site of interest and of the site other than the site of interest. As depicted in FIG. 15, the site of interest is set in an elasticity opacity table 140 created by the elasticity opacity table creating section (elasticity opacity setting section) 16. A site with the intermediate hardness is only infrequently a diagnosis target and is thus set to be the site other than the site of interest. Therefore, the site with the intermediate hardness belonging to an elasticity value range from an elasticity value "a" to an elasticity value "b" is associated with the elasticity opacity as the site other than the site of interest. A hard site and a soft site belonging to the other elasticity value range are associated with the elasticity opacity as the site of interest. Then, the elasticity opacity table creating section (elasticity opacity setting section) 16 sets the elasticity opacity associated with the elasticity value range from the elasticity value "a" to the elasticity value "b" which is the site other than the site of interest to a value smaller than the elasticity opacity associated with the other elasticity value range. The site of interest and the site other than the site of interest are associated with the elasticity opacity in accordance with the purpose.

For example, the elasticity first component volume rendering section 60, the elasticity second component volume rendering section 61, and the elasticity third component volume rendering section 62 in FIG. 6 perform the volume rendering in accordance with Expressions (4) to (6) and use the elasticity opacity as the opacity. In this case, for voxels with elasticity values belonging to the elasticity value range from the elasticity value "a" to the elasticity value "b", the elasticity first component volume rendering section 60, the elasticity second component volume rendering section 61, and the elasticity third component volume rendering section 62 set a shading weight component of "1.0" to disable the effect of the shading.

Specifically, for "a≤E(i)≤b" in Expression (4) for the volume rendering, the shading weight component S(i) is changed to "S(i)=1.0" to disable the shading. On the other hand, for "E(i)<a" or "b<E(i)", the shading weight component S(i) is unchanged at "S(i)=S(i)" to enable the shading.

In this manner, increasing the elasticity opacity of an optionally set site of interest enables construction of a stereoscopic three-dimensional elasticity image for which the shading is enabled. Reducing the elasticity opacity of the site other than the site of interest enables construction of a visually good, translucent three-dimensional elasticity image for which the shading is disabled. As a result, the site of interest can be constructed as a noticeable three-dimensional elasticity image. Since the shading of the site of interest is enabled, the elasticity opacity of the site of interest can be freely set. For example, as depicted in FIG. 15, in the elasticity opacity table 140, the elasticity opacity of a soft site that is a site of interest (an elasticity value range equal to or larger than the elasticity value "b") increases slowly, and the site of interest has a relatively low elasticity opacity with a value closer to the value of the elasticity opacity of the site other than the site of interest. However, setting the elasticity value "b" enables the site of interest and the site other than the site of interest to be reliably distinguished from each other.

As described above, the three-dimensional image constructing section 170 may disable the shading of a portion having a smaller or larger elasticity value than the elasticity value of the site of interest based on the elasticity value (elasticity value range) of the optionally set site of interest. For example, the three-dimensional elasticity image constructing section 17 disables the shading of the site other than the site of interest based on at least one of the elasticity value of the site of interest and the elasticity value of the site other than the site of interest. In this case, as depicted in FIG. 15, the elasticity opacity table creating section (elasticity opacity setting section) 16 may associate an elasticity opacity smaller than the elasticity opacity associated with the elasticity value of the site of interest, with the site other than the site of interest. Since the site of interest and the site other than the site of interest are optionally set based on the elasticity value, a stereoscopic three-dimensional elasticity image for which the shading is enabled can be constructed for the site of interest, and a visually good, translucent three-dimensional elasticity image for which the shading is disabled can be constructed for the site other than the site of interest, regardless of the elasticity opacity. Also in this case, enabling/disabling of the shading of the site other than the site of interest may be controlled.

Furthermore, the three-dimensional cross-section region image constructing section 13 may disable the shading of at least one of a plurality of primary color components (for example, RGB components) for a portion with at least one of a predetermined cross-section region opacity according to the luminance value and a predetermined luminance value.

Furthermore, a method of displaying an ultrasound image for the ultrasound diagnostic apparatus in the above-described embodiment is a method of displaying an ultrasound image involving sending an ultrasonic wave to a diagnosing object 1 via an ultrasound probe 2, receiving a reflected echo signal from the diagnosing object 1, performing the volume rendering with shading on elasticity volume data with an elasticity value based on the reflected echo signal to construct a three-dimensional elasticity image, and displaying the three-dimensional elasticity image, in which the volume rendering is performed using the elasticity opacity according to the elasticity value, and the shading of a portion with the elasticity opacity with a predetermined value is disabled.

Additionally, the method of displaying an ultrasonic wave image for the ultrasound diagnostic apparatus in the above-described embodiment is a method of displaying an ultrasound image involving sending an ultrasonic wave to the diagnosing object 1 via the ultrasound probe 2, receiving a reflected echo signal from the diagnosing object 1, performing the volume rendering with shading on elasticity volume data with an elasticity value based on the reflected echo signal to construct a three-dimensional elasticity image, and displaying the three-dimensional elasticity image, in which the shading of a portion with the elasticity value of a predetermined value is disabled.

Additionally, the method of displaying an ultrasound image for the ultrasound diagnostic apparatus in the above-described embodiment is a method of displaying an ultrasound image involving sending an ultrasonic wave to the diagnosing object 1 via the ultrasound probe 2, receiving a reflected echo signal from the diagnosing object 1, creating cross-section region volume data on the diagnosing object 1 based on the reflected echo signal, creating elasticity volume data with an elasticity value based on the reflected echo signal, synthesizing the cross-section region volume data and the elasticity volume data to create synthetic volume data, performing the volume rendering with shading on the synthetic volume data to construct a three-dimensional synthetic image, and displaying the three-dimensional synthetic image, in which the shading is disabled for a portion with at least one of a predetermined cross-section region opacity according to the luminance of the cross-section region volume data, a predetermined elasticity opacity according to the elasticity value, and the elasticity value of a predetermined value.

INDUSTRIAL APPLICABILITY

The ultrasound diagnostic apparatus according to the present invention can disable the shading in the volume rendering based on the elasticity opacity or the elasticity value to construct a visually good three-dimensional image, and is useful as an ultrasound diagnostic apparatus, a method of displaying an ultrasound image, and the like which disable the shading of a predetermined portion.

REFERENCE SIGNS LIST

1 Diagnosing object
2 Ultrasound probe
3 Sending section
4 Receiving section
5 Ultrasound sending and receiving control section
6 Phase matching and adding section
7 Cross-section region image constructing section
8 RF signal frame data storage section
9 Elasticity image constructing section
10 Cross-section region volume data creating section
11 Cross-section region volume primary color component converting section
12 Cross-section region opacity table creating section (cross-section region opacity setting section)
13 Three-dimensional cross-section region image constructing section
14 Elasticity volume data creating section
15 Elasticity volume primary color component converting section
16 Elasticity opacity table creating section (elasticity opacity setting section)
17 Three-dimensional elasticity image constructing section
18 Switching and adding section
19 Image display section
20 Operation section
21 Control section
30 Cross-section region first component volume rendering section
31 Cross-section region second component volume rendering section
32 Cross-section region third component volume rendering section
60 Elasticity first component volume rendering section
61 Elasticity second component volume rendering section
62 Elasticity third component volume rendering section
100 First component synthesizing section
101 Second component synthesizing section
102 Third component synthesizing section
103 Three-dimensional synthetic image constructing section
104 Synthetic first component volume rendering section
105 Synthetic second component volume rendering section
106 Synthetic third component volume rendering section
150 Volume data synthesizing section
170 Three-dimensional image constructing section

The invention claimed is:
1. An ultrasound diagnostic apparatus comprising:
an ultrasound probe:
a processor that is configured to
  send an ultrasonic wave to a diagnosing object via the ultrasound probe;
  receive a reflected echo signal from the diagnosing object; and
  perform volume rendering with shading on elasticity volume data using an elasticity opacity according to an elasticity value with
    the elasticity value $E(i)$ of the i th voxel on the line of sight, a component value $C(i)$ of the i th voxel on the line of sight, and a shading weight component $S(i)$ of the i th voxel on the line of sight, based on the reflected echo signal to construct a three-dimensional elasticity image, by an equation of

$$Cout(i)=Cout(i-1)+(1-Aout(i-1))*A(i)*C(i)*S(i)$$

$$Aout(1)=Aout(i-1)+(1-Aout(i-1))*A(i)$$

$$A(i)=Opacity[E(i)],$$

wherein $Cout(i)$ is a pixel value outputted, and $Aout(i)$ is a numeral whose initial value is 0 and is integrated each time the voxel is passed through, and the volume rendering further comprises disabling the shading of a portion of the i th voxel on the line of sight with the elasticity opacity more transparent than a predetermined value; and
  a display that displays the three-dimensional elasticity image.
2. An ultrasound diagnostic apparatus comprising:
an ultrasound probe:
a processor that is configured to
  send an ultrasonic wave to a diagnosing object via the ultrasound probe;
  receive a reflected echo signal from the diagnosing object; and
  perform volume rendering with shading on elasticity volume data with
    an elasticity value $E(i)$ of the i th voxel on the line of sight, a component value $C(i)$ of the i th voxel on the line of sight, and a shading weight component $S(i)$ of the i th voxel on the line of sight, based on the reflected echo signal to construct a three-dimensional elasticity image, by an equation of $$\text{Cout}(i) = \text{Cout}(i-1) + (1 - A\text{out}(i-1)) * A(i) * C(i) * S(i)$$

$$A\text{out}(1) = A\text{out}(i-1) + (1 - A\text{out}(i-1)) * A(i)$$

$$A(i) = \text{Opacity}[E(i)],$$

wherein Cout(i) is a pixel value outputted, and Aout (i) is a numeral whose initial value is 0 and is integrated each time the voxel is passed through, and the volume rendering further comprises disabling the shading of a portion of the i th voxel on the line of sight with the elasticity value more transparent than a predetermined value; and a display that displays the three-dimensional elasticity image.

3. The ultrasound diagnostic apparatus according to claim 1, wherein the processor:
converts the elasticity volume data into a plurality of primary color components,
performs volume rendering with shading on at least one of the plurality of primary color components to construct a three-dimensional elasticity image, and
disables the shading of at least one of the plurality of primary color components for a portion with at least one of a predetermined elasticity opacity according to the elasticity value and the elasticity value of a predetermined value.

4. The ultrasound diagnostic apparatus according to claim 1, wherein the processor disables the shading when the elasticity opacity is smaller than a preset reference value.

5. The ultrasound diagnostic apparatus according to claim 4, comprising an operation section that adjusts the reference value.

6. The ultrasound diagnostic apparatus according to claim 4, wherein the reference value is set based on a minimum value of the elasticity opacity according to the elasticity value.

7. The ultrasound diagnostic apparatus according to claim 1, wherein the processor associates the elasticity value with the elasticity opacity to set the elasticity opacity according to the elasticity value.

8. The ultrasound diagnostic apparatus according to claim 7, wherein the processor: associates an elasticity opacity smaller than the elasticity opacity associated with a site other than a site of interest, and disables the shading of the site other than the site of interest based on the elasticity value or the elasticity opacity.

9. The ultrasound diagnostic apparatus according to claim 2, wherein the processor disables the shading of a site other than a site of interest based on at least one of the elasticity value of the site of interest and the elasticity value of the site other than the site of interest.

10. The ultrasound diagnostic apparatus according to claim 1, wherein the display switchably displays both or one of the three-dimensional elasticity image for which the shading is disabled and the three-dimensional elasticity image for which the shading is not disabled.

11. The ultrasound diagnostic apparatus according to claim 1, wherein the processor switches to both or one of the three-dimensional elasticity image for which the shading is disabled and the three-dimensional elasticity image for which the shading is not disabled.

12. A method of displaying an ultrasound image, the method comprising:
sending an ultrasonic wave to a diagnosing object via an ultrasound probe;
receiving a reflected echo signal from the diagnosing object;
performing volume rendering with
shading on elasticity volume data with an elasticity value E(i) of the i th voxel on the line of sight,
a component value C(i) of the i th voxel on the line of sight, and
a shading weight component S(i) of the i th voxel on the line of sight,
based on the reflected echo signal to construct a three-dimensional elasticity image, by an equation of $$\text{Cout}(i) = \text{Cout}(i-1) + (1 - A\text{out}(i-1)) * A(i) * C(i) * S(i)$$

$$A\text{out}(1) = A\text{out}(i-1) + (1 - A\text{out}(i-1)) * A(i)$$

$$A(i) = \text{Opacity}[E(i)]; \text{ and}$$

displaying the three-dimensional elasticity image,
wherein
the volume rendering is performed using elasticity opacity according to the elasticity value, and the shading of a portion of the i th voxel on the line of sight with the elasticity opacity more transparent than a predetermined value is disabled,
Cout(i) is a pixel value outputted, and Aout (i) is a numeral whose initial value is 0 and is integrated each time the voxel is passed through, and
the steps of sending, receiving and performing are performed by a processor and the step of displaying is performed by a display.

13. A method of displaying an ultrasound image, the method comprising:
sending an ultrasonic wave to a diagnosing object via an ultrasound probe;
receiving a reflected echo signal from the diagnosing object;
performing volume rendering with shading on elasticity volume data with
an elasticity value E(i) of the i th voxel on the line of sight,
a component value C(i) of the i th voxel on the line of sight, and
a shading weight component S(i) of the i th voxel on the line of sight,
based on the reflected echo signal to construct a three-dimensional elasticity image, by an equation of $$\text{Cout}(i) = \text{Cout}(i-1) + (1 - A\text{out}(i-1)) * A(i) * C(i) * S(i)$$

$$A\text{out}(1) = A\text{out}(i-1) + (1 - A\text{out}(i-1)) * A(i)$$

$$A(i) = \text{Opacity}[E(i)]; \text{ and}$$

displaying the three-dimensional elasticity image,
wherein
the shading of a portion of the i th voxel on the line of sight with the elasticity value more transparent than a predetermined value is disabled,
Cout(i) is a pixel value outputted, and
Aout (i) is a numeral whose initial value is 0 and is integrated each time the voxel is passed through, and
the steps of sending, receiving and performing are performed by a processor and the step of displaying is performed by a display.

14. The ultrasound diagnostic apparatus according to claim 2, wherein the processor converts the elasticity volume data into a plurality of primary color components, performs volume rendering with shading on at least one of the plurality of primary color components to construct a three-dimensional elasticity image, and disables the shading of at least one of the plurality of primary color components for a portion with at least one of a predetermined elasticity opacity according to the elasticity value and the elasticity value of a predetermined value.

15. The ultrasound diagnostic apparatus according to claim 2, wherein the display switchably displays both or one of the three-dimensional elasticity image for which the shading is disabled and the three-dimensional elasticity image for which the shading is not disabled.

16. The ultrasound diagnostic apparatus according to claim 2, the processor switches to both or one of the three-dimensional elasticity image for which the shading is disabled and the three-dimensional elasticity image for which the shading is not disabled.

* * * * *